(12) United States Patent
Rocha-Singh (10) Patent No.: US 9,370,644 B2
(45) Date of Patent: Jun. 21, 2016

(54) APPARATUS AND METHOD FOR DELIVERING INTRALUMINAL THERAPY

(71) Applicant: Krishna Rocha-Singh, Springfield, IL (US)

(72) Inventor: Krishna Rocha-Singh, Springfield, IL (US)

(*) Notice: Subject to any disclaimer, the term of this patent is extended or adjusted under 35 U.S.C. 154(b) by 27 days.

(21) Appl. No.: 14/477,638

(22) Filed: Sep. 4, 2014

(65) Prior Publication Data

US 2014/0378890 A1    Dec. 25, 2014

Related U.S. Application Data

(62) Division of application No. 14/084,518, filed on Nov. 19, 2013, now Pat. No. 8,827,953.

(60) Provisional application No. 61/752,902, filed on Jan. 15, 2013.

(51) Int. Cl.
*A61M 25/10* (2013.01)
*A61B 17/22* (2006.01)
(Continued)

(52) U.S. Cl.
CPC ........ *A61M 25/1002* (2013.01); *A61B 17/2202* (2013.01); *A61F 7/007* (2013.01);
(Continued)

(58) Field of Classification Search
CPC ............ A61M 25/10; A61M 25/1011; A61M 2025/1013; A61M 2025/1015; A61M 2025/1086; A61M 2025/1088; A61M 2025/105; A61M 2025/1072
See application file for complete search history.

(56) References Cited

U.S. PATENT DOCUMENTS

| 1,690,995 A | 11/1928 | Pratt |
| 4,233,983 A | 11/1980 | Rocco |

(Continued)

FOREIGN PATENT DOCUMENTS

| EP | 2 495 007 A1 | 9/2012 |
| WO | WO-96/13298 A1 | 5/1996 |
| WO | WO-2011/141866 A2 | 11/2011 |

OTHER PUBLICATIONS

PCT International Search Report and Written Opinion dated Apr. 4, 2014 in related PCT Application No. PCT/US2014/010095.

*Primary Examiner* — Quynh-Nhu H Vu
(74) *Attorney, Agent, or Firm* — Foley & Lardner LLP; Christopher C. Bolten; Nicola A. Pisano (57) ABSTRACT

A catheter and methods for luminal therapy are provided wherein a catheter has an outer balloon with a multiplicity of apertures for infusing one or more therapeutic agents into a vessel wall, an intermediate balloon having a multiplicity of apertures offset from the apertures of outer balloon to serve as a baffle that reduces jetting and promotes uniform distribution of therapeutic agent exiting through the outer balloon, and an impermeable inner balloon disposed within the intermediate balloon that enables the intermediate and outer balloons to be forced into engagement with the vessel wall to dilate the vessel and disrupt plaque lining the vessel wall and to also facilitate the uniform delivery of the therapeutic agent. The outer balloon may include protrusions that contact the vessel wall to disrupt the plaque, bumpers to reduce washout during infusion of therapeutic agents; the intermediate balloon may include a texture, ribs or protrusions on its outer surface to prevent adhesion to the outer balloon during dilation of the vessel; and the catheter may include a guide wire lumen sized to accept an energy delivery device to delivery energy that enhances uptake of the therapeutic agent or prolongs therapeutic effectiveness of the agent.

20 Claims, 7 Drawing Sheets

(51) Int. Cl.
   *A61N 5/06*         (2006.01)
   *A61F 7/00*         (2006.01)
   *A61N 7/00*         (2006.01)

(52) U.S. Cl.
   CPC ........ *A61M 25/104* (2013.01); *A61M 25/1011* (2013.01); *A61N 5/062* (2013.01); *A61N 7/00* (2013.01); *A61F 2007/0071* (2013.01); *A61M 2025/105* (2013.01); *A61M 2025/1013* (2013.01); *A61M 2025/1015* (2013.01); *A61M 2025/1031* (2013.01); *A61M 2025/1086* (2013.01); *A61N 2005/0661* (2013.01)

(56) References Cited

U.S. PATENT DOCUMENTS

| | | |
|---|---|---|
| 4,417,576 A * | 11/1983 | Baran .................... A61M 16/04 128/207.15 |
| 4,581,017 A | 4/1986 | Sahota |
| 4,590,211 A | 5/1986 | Voorhees et al. |
| 4,762,130 A | 8/1988 | Fogarty et al. |
| 4,994,033 A | 2/1991 | Shockey et al. |
| 5,037,392 A | 8/1991 | Hillstead |
| 5,049,132 A | 9/1991 | Shaffer et al. |
| 5,071,406 A | 12/1991 | Jang |
| 5,100,429 A | 3/1992 | Sinofsky et al. |
| 5,112,305 A | 5/1992 | Barath et al. |
| 5,163,989 A | 11/1992 | Campbell et al. |
| 5,196,024 A | 3/1993 | Barath |
| 5,213,576 A | 5/1993 | Abiuso et al. |
| 5,226,887 A | 7/1993 | Farr et al. |
| 5,254,089 A | 10/1993 | Wang |
| 5,336,178 A | 8/1994 | Kaplan et al. |
| 5,336,234 A | 8/1994 | Vigil et al. |
| 5,423,745 A * | 6/1995 | Todd et al. .................... 604/500 |
| 5,425,723 A | 6/1995 | Wang |
| 5,571,086 A | 11/1996 | Kaplan et al. |
| 5,599,306 A | 2/1997 | Klein et al. |
| 5,611,775 A | 3/1997 | Machold et al. |
| 5,653,689 A | 8/1997 | Buelna et al. |
| 5,653,690 A | 8/1997 | Booth et al. |
| 5,662,712 A * | 9/1997 | Pathak et al. .............. 623/23.64 |
| 5,665,063 A | 9/1997 | Roth et al. |
| 5,674,287 A | 10/1997 | Slepian et al. |
| 5,681,281 A | 10/1997 | Vigil et al. |
| 5,718,684 A | 2/1998 | Gupta |
| 5,749,915 A | 5/1998 | Slepian |
| 5,797,935 A | 8/1998 | Barath |
| 5,800,408 A | 9/1998 | Strauss et al. |
| 5,800,538 A | 9/1998 | Slepian et al. |
| 5,810,767 A | 9/1998 | Klein |
| 5,833,658 A * | 11/1998 | Levy et al. .................. 604/97.01 |
| 5,873,852 A | 2/1999 | Vigil et al. |
| 5,899,917 A | 5/1999 | Edwards et al. |
| 6,013,055 A | 1/2000 | Bampos et al. |
| 6,048,332 A | 4/2000 | Duffy et al. |
| 6,129,706 A | 10/2000 | Janacek |
| 6,136,011 A * | 10/2000 | Stambaugh ............ A61F 2/958 604/101.02 |
| 6,210,392 B1 | 4/2001 | Vigil et al. |
| 6,287,320 B1 | 9/2001 | Slepian |
| 6,544,224 B1 | 4/2003 | Steese-Bradley |
| 6,632,231 B2 | 10/2003 | Radisch, Jr. |
| 6,635,027 B1 | 10/2003 | Cragg et al. |
| 6,733,474 B2 | 5/2004 | Kusleika |
| 7,008,438 B2 | 3/2006 | O'Brien |
| 7,018,358 B2 | 3/2006 | Joergensen et al. |
| 7,070,606 B2 | 7/2006 | Seward |
| 7,115,299 B2 * | 10/2006 | Kokish ........................ 427/2.24 |
| 7,160,317 B2 | 1/2007 | Mc Hale et al. |
| 7,270,673 B2 | 9/2007 | Yee et al. |
| 7,566,319 B2 | 7/2009 | McAuley et al. |
| 7,686,824 B2 | 3/2010 | Konstantino et al. |
| 7,887,557 B2 | 2/2011 | Kelley et al. |
| 7,942,848 B2 * | 5/2011 | Rahimsobhani ......... 604/101.02 |
| 8,088,100 B2 | 1/2012 | Blix |
| 8,187,221 B2 | 5/2012 | Bates |
| 8,192,675 B2 | 6/2012 | Burton et al. |
| 8,211,354 B2 | 7/2012 | Burton |
| 8,317,747 B2 | 11/2012 | Kusleika |
| 2002/0032406 A1 * | 3/2002 | Kusleika ............ A61M 25/1011 604/101.02 |
| 2004/0260239 A1 | 12/2004 | Kusleika |
| 2007/0066961 A1 | 3/2007 | Rutter |
| 2009/0254064 A1 * | 10/2009 | Boatman ....................... 604/509 |
| 2009/0254113 A1 | 10/2009 | Nolan et al. |
| 2010/0010470 A1 | 1/2010 | Bates |
| 2010/0331817 A1 * | 12/2010 | Schaeffer .......... A61M 25/1011 604/509 |
| 2012/0071715 A1 | 3/2012 | Beyar et al. |
| 2012/0150142 A1 | 6/2012 | Weber et al. |

* cited by examiner

APPARATUS AND METHOD FOR DELIVERING INTRALUMINAL THERAPY

CROSS-REFERENCE TO RELATED APPLICATIONS

This application is a divisional under 35 U.S.C. §120 of U.S. patent application Ser. No. 14/084,518, filed Nov. 19, 2013, now U.S. Pat. No. 8,827,953, issued Sep. 9, 2014, which claims the benefit of priority of U.S. Provisional Patent Application Ser. No. 61/752,902, filed Jan. 15, 2013, the entire contents of both of which are incorporated herein by reference.

FIELD OF THE INVENTION

The present invention relates generally to the delivery of intraluminal therapy, such as treatment of vascular lesions. In some preferred embodiments, apparatus and methods are provided for treating calcified lesions in peripheral vasculature to prevent arterial dissections, atheroembolizations, perforations and restenosis following an angioplasty and/or stent procedures.

BACKGROUND OF THE INVENTION

A need exists for simple and efficacious delivery of intraluminal therapies. Such therapies range from delivery of antimitotic agents to reduce the restenosis following angioplasty, to delivery of angiogenic factors, delivery of therapeutic agents to reduce intravascular thrombus, delivery of therapeutic agents to improve arterial compliance through the structural alteration of intimal and medial calcification, delivery of fluent cross-linkable materials that may be hardened in situ to provide support for a vessel (e.g., as is described in U.S. Pat. No. 5,749,915 to Slepian, the entire contents of which is incorporated herein by reference), or to exclude or reduce the development of a nascent vascular aneurysms. Previously-known methods and apparatus typically involve use of multiple catheters and devices to accomplish such treatments, which adds time, cost and complexity, increased exposure to ionizing radiation and risk of morbidity to previously-known therapeutic procedures. It therefore would be advantageous to provide methods and apparatus that simplify such previously-known procedures, reduce time, cost and complexity, and improve acute procedural success and long-term patient outcomes.

Percutaneous transluminal angioplasty of coronary and peripheral arteries (PTCA and PTA, respectively) are widely accepted as the revascularization procedures of choice in patients with ischemic cardiovascular syndromes (i.e., chronic and acute coronary ischemic syndromes and chronic limb ischemia, including claudication and critical limb ischemia). However, use of these conventional percutaneous treatments has an important limitation: restenosis—the exuberant proliferation of smooth muscle cells that grow to re-occlude the treated vessel segment, causing the reoccurrence of symptoms and necessitating potential reintervention.

Various adjuncts to angioplasty seek to reduce restenosis; these include atherectomy (e.g., extractional, rotational, orbital, laser), bare metal and bare nitinol stents and, more recently, drug eluting stents (DES). The latter technology has been demonstrated to significantly reduce coronary artery restenosis when compared to angioplasty or bare metal stents, however, its use requires chronic administration of adjunct pharmacotherapies to prevent subacute stent thrombosis, the sudden and life threatening clotting of the stent. Unfortunately, not all patients tolerate these essential pharmacotherapies due to impaired tolerance, allergic reactions or contraindication to such drug use (i.e., history of previous bleeding) and/or their associated expense.

In peripheral arteries, the use of bare nitinol stents have been shown to be superior to balloon angioplasty alone and has emerged as the "default" percutaneous strategy for the treatment of chronic limb ischemic syndromes, particularly in complex disease patterns involving the femoropopliteal artery. Despite their common use, nitinol stents present a substantial concern of in-stent restenosis (ISR), the proliferation of smooth muscle cells within the stent leading to occlusion of the stent lumen. ISR poses additional risk to the patient by necessitating additional vessel reintervention to re-establish vessel blood flow.

Currently, there is no established treatment for the vexing problem of ISR, which occurs in about 30%-50% of nitinol stents over a 1-2 year follow-up period, a rate that may increase depending on the patient demographic (i.e., diabetics) and vessel morphology (small vessel diameter, length of diseased vessel treated and the presence of vessel wall calcification). Importantly, there are presently no recognized effective and durable therapies to treat ISR; as such, emerging technologies focus on preventing restenosis through the application of anti-restenotic therapeutic agents into the diseased vessel wall layers via the vessel's luminal surface.

Anti-proliferative drugs (i.e., paclitaxel, sirolimus) retard smooth muscle migration into an area of angioplasty-induced vessel injury and reduce restenosis. Drug delivery catheters have been designed to facilitate the delivery of such therapeutic agents into the vessel wall via its luminal surface. For example, U.S. Pat. No. 5,112,305 to Barath et al. describes a catheter having a single balloon including a multiplicity of protrusions. The protrusions include apertures that enable a drug to be introduced into the balloon and infused through the apertures into the vessel wall. U.S. Pat. No. 5,049,132 to Shaffer et al. and U.S. Pat. No. 6,733,474 to Kusleika each describe a catheter having an impermeable inner balloon and an outer balloon having pores through which a drug may be infused into the vessel wall. U.S. Pat. No. 5,681,281 to Vigil et al. similarly shows a catheter having an impermeable inner balloon and an outer balloon having a multiplicity of apertured protrusions for injecting a drug into a vessel wall. U.S. Pat. No. 5,213,576 to Abiuso et al. describes a catheter having nested balloons with offset apertures, to reduce jetting and provide more uniform distribution of a drug infused into a vessel through the catheter.

All of the previously-known systems described in the foregoing patents have had drawbacks that have prevented commercialization of those designs. For example, catheters having a single apertured balloon, such as described in the above patent to Shaffer et al., cannot provide uniform distribution of a drug or other material around the circumference or along the axis of the vessel due to jetting through the apertures. Catheters with apertured protrusions, such as described in the above patents to Barath et al. and Vigil et al, are difficult to manufacture and are believed to be prone to having the apertures clogged with debris when the balloon is embedded into the plaque lining the vessel wall. Also, the use of excessively high pressures within the balloon to clear the apertured protrusions may lead to excessively non-uniform drug infusion and potential vessel dissection.

On the other hand, in a catheter such as described in Abiuso et al., nested balloons having offset apertures cause the inner balloon to serve as a baffle that reduces jetting through the apertures in the outer balloon, thereby providing a much more uniform infusion through the outer balloon. However, as the Abiuso catheter lacks an inner impermeable balloon to move the drug infusing layers into apposition with the vessel wall, there is the potential for much of the drug to be washed into systemic circulation during deployment of the nested balloons. Moreover, because Abiuso lacks a dilatation balloon, it has no ability to disrupt calcified plaque, and accordingly, must be used with a separate dilatation balloon requiring additional catheter exchanges, contrast and radiation exposure and vessel irritation.

Recent clinical data has identified a variety of atherosclerotic plaque morphologies in coronary and peripheral vessels, which prevent the effective penetration of drug therapies into the various vessel layers. Specifically, the presence of dense fibro-calcific and calcified intimal and medial plaques, are associated with peri-procedural failure (due to vessel recoil and/or vessel wall dissection) and subsequent restenosis as these plaques are effective barriers to the penetration and uptake of therapeutic drugs delivered luminally. As such, the instructions for use (IFU) of many current approved devices and inclusion/exclusion angiographic criteria of on-going regulatory trial designs specifically exclude patients from device treatment with angiographic evidence of severely calcified vessels. Given the large and growing patient population with diabetes and chronic kidney disease and conditions associated with heavy vessel wall calcification, this represents a substantial patient population in which emerging therapies may be ineffective.

In view of the many drawbacks of previously-known systems and methods, it would be desirable to provide apparatus and methods that overcome such drawbacks. In particular, it would be desirable to provide devices suitable for intraluminal therapies, such as intravascular drug infusion systems and methods, which reduce the number of equipment exchanges needed to both disrupt intravascular plaque and to infuse an anti-stenotic agent into a vessel wall to reduce occurrence of restenosis.

It further would be desirable to provide devices and methods suitable for intraluminal therapies, such as intravascular drug infusion systems and methods, that permit a clinician to dilate a vessel to disrupt calcified plaque and then to infuse an anti-mitotic agent into the vessel wall through the disrupted plaque.

It still further would be desirable to provide devices and methods suitable for intraluminal therapies, such as intravascular drug infusion systems and methods, wherein a balloon of the catheter may include a multiplicity of apertures, such that the apertures are resistant to clogging during use of the balloon to dilate the vessel and disrupt the plaque.

Previously known systems also describe the use of various energy sources to deliver energy to fluent material infused into a vessel to pave a vessel or create an in situ stent. Such systems are described, for example, in U.S. Pat. No. 5,662,712 to Pathak et al. and U.S. Pat. No. 5,899,917 to Edwards et al. A drawback of these systems, however, is that each forms a new mechanical structure disposed within the vessel that is separate and distinct from the vessel wall. Because the arteries, and to a lesser extent, the veins, expand and contract during each cardiac cycle due to pressure pulsations, such attempts to form a rigid mechanical support that is not integrated with the vessel wall are inherently problematic.

It therefore further would be desirable to use existing vasculature structure to enhance or perpetuate the anti-mitotic effect of drugs infused via an intravascular route. In particular, it would be desirable to employ application of energy, e.g., such as ultraviolet (UV) light energy, monopolar or bipolar generated radiofrequency (RF) generated heat, or focused or unfocused ultrasonic energy, to potentiate the delivery and effectiveness of anti-mitotic agents when administered from the luminal surface into the media and adventitial layers in the presence of vascular calcification.

SUMMARY OF THE INVENTION

In view of the aforementioned drawbacks of previously-known systems and methods, the present invention provides apparatus and methods that reduce the number of equipment exchanges needed to both disrupt intravascular plaque and to infuse therapeutic agents, such as anti-proliferative drugs or regenerative therapy agents, into a vessel wall to reduce occurrence of restenosis and/or promote angiogenesis, or to exclude a weakened vessel portion or reduce enlargement of a nascent aneurysm.

The present invention further provides devices and methods suitable for intraluminal therapies, such as intravascular drug infusion systems and methods, that permit a clinician to dilate a vessel to disrupt calcified plaque and then to infuse therapeutic agents into the vessel wall through the disrupted plaque without the need to exchange catheters.

In accordance with another aspect of the present invention, a balloon catheter is provided including an outer balloon having a multiplicity of apertures for infusing one or more therapeutic agents into the vessel wall, an intermediate balloon having a multiplicity of apertures offset from the apertures of outer balloon to serve as a baffle that reduces jetting and promotes uniform distribution of therapeutic agents through the outer balloon, and an impermeable inner balloon disposed within the intermediate balloon that enables the intermediate and outer balloons to be forced into engagement with the vessel wall to dilate the vessel and disrupt plaque lining the vessel wall.

The intermediate balloon optionally may include a texture, ribs or protrusions on its outer surface that contacts the inner surface of the outer balloon to prevent the intermediate and outer balloons from adhering to one another during dilation of the vessel. Such a feature ensures that an annular space is maintained between the intermediate and outer balloons to facilitate uniform distribution of therapeutic agents during use of the catheter to perform therapy.

The outer balloon also may include bumpers at its proximal and distal ends to facilitate delivery of therapeutic agents. The outer balloon optionally may include a multiplicity of protrusions and apertures, such that the apertures are interposed between the protrusions so as to reduce the risk that the apertures become clogged during use of the balloon to dilate the vessel and disrupt the plaque.

In accordance with yet another aspect of the present invention, a catheter of the present invention is constructed to include a central lumen that accommodates not only a conventional guide wire for positioning the catheter, but also permits a wire carrying an energy source, such as an ultraviolet light source ("UV"), ultrasound transducer, electrically-powered resistive heater, or monopolar or bipolar radiofrequency (RF) heating element, to be substituted for the guide wire to deliver energy to the vessel wall segment where the therapeutic agent was infused. In a preferred embodiment, the material comprising the distal end region of the catheter shaft, and preferably also the materials comprising the inner, intermediate and outer balloons, are selected to reduce absorption energy delivered to the material infused into the vessel wall.

Methods of using the apparatus of the present invention also are provided, wherein the inventive catheter is first used, by inflating the inner balloon with a conventional balloon inflation system, to dilate a vessel and disrupt calcified plaque disposed on the luminal lining. The inner balloon is then depressurized, and one or more suitable fluent therapeutic agents are infused into a space between the inner balloon and the intermediate balloon. The therapeutic agent passes through the multiplicity of apertures, designed of specific variable diameters and positioned in specific patterns along the inner-most and outer-most balloons, into the annular space between the intermediate and outer balloons, and then through the apertures in the outer balloon to uniformly contact the disrupted plaque. Immediately, or after a predetermined interval, an energy delivery source, (e.g., a wire delivering a UV light source, ultrasound transducer or resistive heater), may be exchanged for the guide wire in the central lumen of the catheter. The energy source is activated to enhance uptake of the therapeutic agent through plaque, intima, media of the vessel wall so that the therapeutic agent becomes deposited in the media, adventitia and/or vaso vasorum of the vessel wall, or to activate a property of the fluent material to cause it to harden or otherwise transition to effectuate a therapeutic or diagnostic purpose.

In accordance with one aspect of the present invention, the application of energy from the energy source to the therapeutic agent infused into the vessel wall causes the agent to polymerize in the adventitia or vaso vasorum, thereby reducing washout of the drug caused by circulation through the vaso vasorum. In this manner, the therapeutic agent will be localized within the vessel wall, and serve as a reservoir that prolongs the therapeutic effect of the agent, for example, by reducing occurrence of late-term restenosis of the vessel. Alternatively, the agent may polymerize to form a durable rigid or semi-rigid support within the vessel wall, that serves as an in situ stent that reduces reduction (restenosis) or enlargement (growth of an aneurysm) of the vessel diameter, as suited for a particular therapy. Alternatively, energy from the energy source may be delivered to the vessel media, adventitia and/or vaso vasorum prior to the application of the therapeutic agent or substance.

The apparatus and methods of the present invention therefore facilitate ease of use by reducing the number of catheters required for the effective pre-dilatation of a diseased vessel segment and facilitates the penetration and controlled, uniform delivery of one or more therapeutic agents into the vessel layers using a baffled balloon, which may include a multiplicity of bumpers or protrusions configured to disrupt calcified plaque while avoiding clogging of the infusion apertures. Finally, the catheter provides a central lumen dimensioned to accept an externally powered energy source, and the distal region of the catheter preferably comprises materials that facilitate transmission of such energy to the therapeutic agent while reducing absorption by the catheter materials.

BRIEF DESCRIPTION OF THE DRAWINGS

Further features of the invention, its nature and various advantages will be apparent from the accompanying drawings and the following detailed description of the preferred embodiments, in which.

DETAILED DESCRIPTION OF THE PREFERRED EMBODIMENTS

Figure 1:
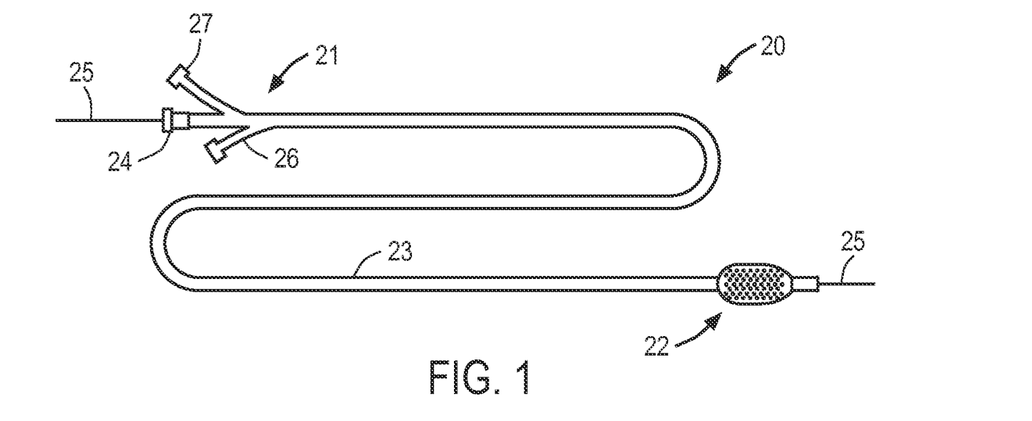
FIG. 1 is a plan view of the illustrative catheter constructed in accordance with the principles of the present invention.

Referring to FIG. 1, balloon catheter 20 constructed in accordance with the principles of the present invention is described. Catheter 20 includes proximal end 21, distal region 22 and elongated shaft 23. Proximal end 21, which is manipulated by the clinician, preferably includes hemostatic port 24 that permits conventional guide wire 25 to be extended through a lumen of catheter 20, balloon inflation port 26 and infusion agent port 27. Catheter preferably has a length and diameter suitable for use in the desired cardiac or peripheral vessel, e.g., 130 to 150 cm in length with a diameter of 2.5 mm to 60 mm, in the case of an abdominal aortic or thoracic aneurysm and balloon lengths from 2 cm to 20 cm. Ports 24, 26 and 27 are conventional elements, and together with proximal end 21 of catheter 20 may comprise materials conventionally used in the construction of intravascular catheters, e.g., polyethylene or polyterephthalate. Although catheter 20 is depicted as an over-the-wire ("OTW") catheter, it is to be understood that the inventive aspects of the catheter of the present invention readily may be employed in a rapid exchange ("RX") catheter or in a catheter having a working lumen and an auxiliary lumen for guidewire insertion such as that described in U.S. Pat. No. 7,018,358 to Joergensen, the entire contents of which is incorporated herein by reference.

Figure 2A:
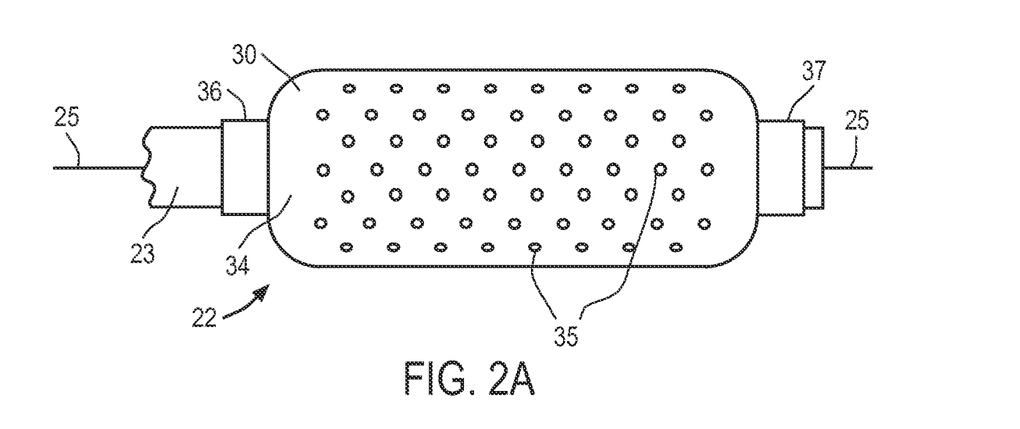
FIGS. 2A and 2B are, respectively, detailed plan and sectional views of the distal region of the catheter of FIG. 1.
Figure 2B:
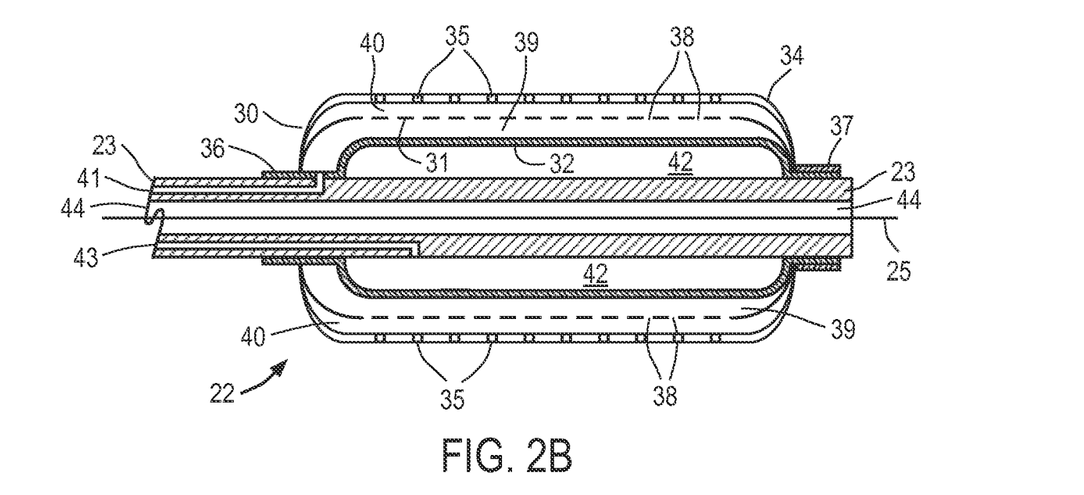

Referring now to FIGS. 2A and 2B, distal region 22 of one embodiment of catheter 20 of the present invention is described. FIG. 2A depicts the exterior of distal region 22 with outer balloon 30 in an expanded state suitable for dilating a vessel, while for purposes of clarity, FIG. 2B depicts a sectional view of the inner components of distal region 22 with intermediate balloon 31 and inner balloon 32 in partially expanded states suitable for infusing a therapeutic agent into a vessel wall. Outer balloon 30 preferably comprises a non-compliant or semi-compliant material such as polyethylene or polyterephthalate. Outer balloon 30 is sized and shape for insertion as appropriate for the intended therapy and bodily lumen. For example, outer balloon 30 may have a diameter in an expanded state of about 2.5-4.0 mm for insertion in smaller lumens, such as coronary vessels, about 4-7 mm for insertion in larger lumens such as peripheral vessels, or as much as 4-6 cm if the catheter is designed for use in providing therapy in the thoracic or abdominal aorta. Intermediate balloon 31 and inner balloon 32 preferably comprise a semi-compliant or compliant material such as polyterephthalate or nylon. As described in further detail below, in a preferred embodiment, inner balloon 32 is configured to expand intermediate balloon 31 and outer balloon 30 until outer balloon 30 reaches its maximum designed diameter. In an alternative embodiment, outer balloon 30 also may comprise a compliant material, while intermediate balloon 31 and inner balloon 32 also may comprise a non-compliant material.

Still referring to FIGS. 2A and 2B, outer balloon 30 has exterior surface 34 and multiplicity of through-wall apertures 35. In the embodiment depicted in FIG. 2A, apertures 35 illustratively are arranged in a pattern where each row is offset by a predetermined angle, e.g., about 45°, from an adjacent row; however, other patterns will readily occur to a person of ordinary skill in the design of balloon catheters. For example, each row or pattern of apertures on the outer balloon may be aligned uniformly with adjacent rows; there may be a single row of apertures on the outer balloon; there may be two rows of apertures on opposite sides of the outer balloon, etc. In addition, apertures 35 are depicted as being circular in shape which may vary in diameter along the length of the balloon, but could have any other desired shapes, such as rectangular, triangular or elliptical. Outer balloon 30, intermediate balloon 31 and inner balloon 32 preferably are affixed to catheter shaft 23 at shoulders 36 and 37 via thermal bonds or glue welds.

As best shown in FIG. 2B, intermediate balloon 31 includes multiplicity of through-wall apertures 38 which may have varying diameters along the balloon length, and which preferably are offset from apertures 35 in outer balloon 30. In this manner, a fluent therapeutic agent introduced into annular space 39 between the exterior of inner balloon 32 and interior surface of intermediate balloon 31 will pass into annular space 40 between the exterior of intermediate balloon 31 and the interior surface of outer balloon 30 without directly exiting through apertures 35 in the outer balloon. Accordingly, when a therapeutic agent is introduced into annular space 39 via infusion lumen 41 and infusion port 27 on proximal end 21 (see FIG. 1), the agent passes from annular space 39 to annular space 40, from which it uniformly exits outer balloon 30 via apertures 35. Inflation port 26 on proximal end 21 (see FIG. 1) is coupled to interior space 42 of inner balloon 32 via inflation lumen 43 that extends through catheter shaft 23. Apertures 35 may be the same size or a different size than apertures 38. Preferably, apertures 35 and 38 are laser drilled and have a diameter between about 5 μm and about 50 μm. In one embodiment, apertures 35 have a diameter of about 5 μm and apertures 38 have a diameter of about 10 μm. In addition, a subset of the multiplicity of apertures 35 or 38 may be differently sized from another subset of the multiplicity. For example, a distal portion of a row of apertures 35 each may have a first diameter and a proximal portion of the row each may have a second diameter, different from the first. In one embodiment, in a row of sixteen apertures, eight distal apertures each has a diameter of about 15-25 μm and eight proximal apertures each has a diameter of about 7-17 μm.

As depicted in FIG. 2B, after use of catheter 20 for dilating the vessel wall, inner balloon 32 may be inflated to any lower desired pressure to reduce the volume of therapeutic agent delivered into annular space 39 and to facilitate the rate of delivery to the vessel wall. Alternatively, inner balloon 32 may be deflated entirely after the vessel dilatation step.

Still referring to FIG. 2B, catheter shaft 23 includes lumen 44, preferably centrally located in catheter shaft 23, to permit guide wire 25 to be extended through catheter 20 to facilitate positioning of distal region 22 at a desired location in a patient's vasculature or organ. Distal region 22 also may include radiopaque markers disposed along catheter shaft 23, for example, in the vicinity of shoulders 36 and 37, to facilitate positioning of the catheter under fluoroscopic imaging. In accordance with one aspect of the present invention, lumen 44 preferably is sized to permit a wire containing an energy source, e.g., an ultraviolet light source (or light fiber), ultrasound transducer, or resistive heater, to be advanced into distal region 22 to deposit energy into the therapeutic agent or drug, to facilitate uptake by the vessel wall or provide another therapeutic effect, as described herein below. For such embodiments, balloons 30-31 and catheter shaft 23 preferably comprise materials that permit light energy of selected frequencies to pass through the catheter without significant absorption or loss of energy.

Figure 3A:
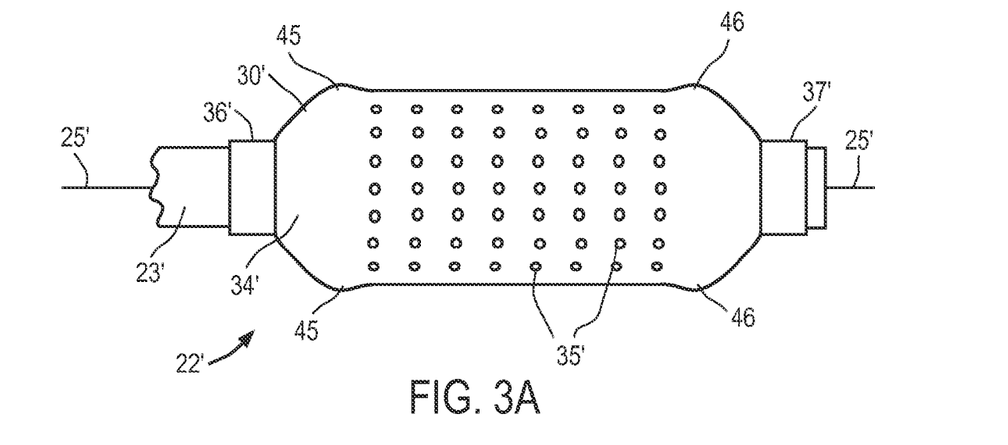
FIGS. 3A and 3B are, respectively, detailed plan and sectional views of the distal region of an alternative catheter constructed in accordance with the principles of the present invention.
Figure 3B:
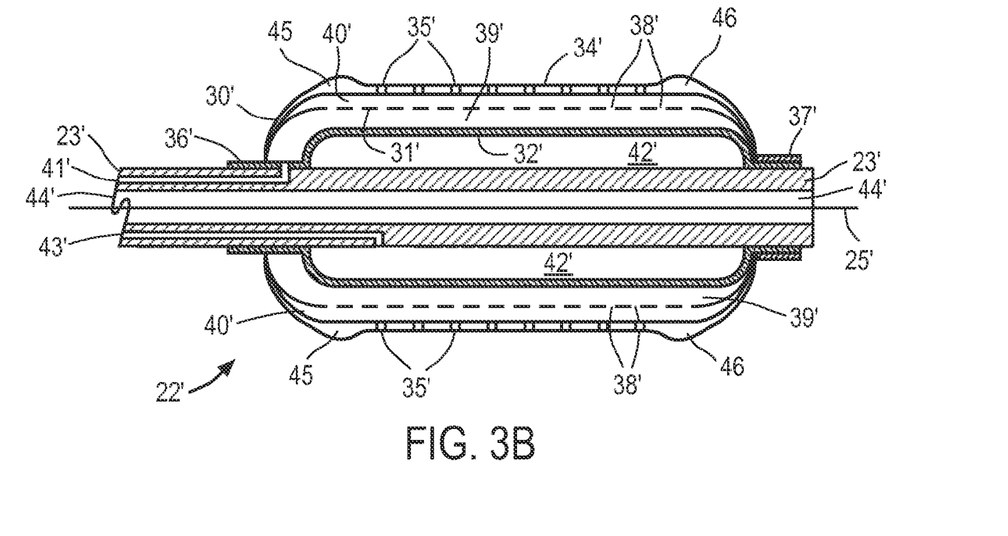

Referring now to FIGS. 3A and 3B, distal region 22' of an alternative balloon catheter is constructed similarly to distal region 22 of FIGS. 2A and 2B, wherein like components are identified by like-primed reference numbers. Thus, for example, apertures 35' in FIGS. 3A and 3B correspond to apertures 35 of FIGS. 2A and 2B, etc. As will be observed by comparing FIGS. 2A, 2B and 3A, 3B, outer balloon 30' includes proximal bumper 45 around the circumference of its proximal end and distal bumper 46 around the circumference of its distal end, and apertures 35' are aligned in uniform rows. Bumpers 45, 46 extend from exterior surface 34' so as to create a pocket between bumpers 45 and 46 and between exterior surface 34' and the luminal surface when bumpers 45, 46 are urged into contact with the luminal surface. In this manner, bumpers 45, 46 facilitate delivery of therapeutic agents to the luminal surface via the pocket such that the agents are delivered uniformly along the length of the balloon, reduce clogging of the apertures when the bumpers are urged into contact with the luminal surface, and reduce the risk that fluent material delivered to the vessel surface will be washed into systemic circulation.

Figure 4A:
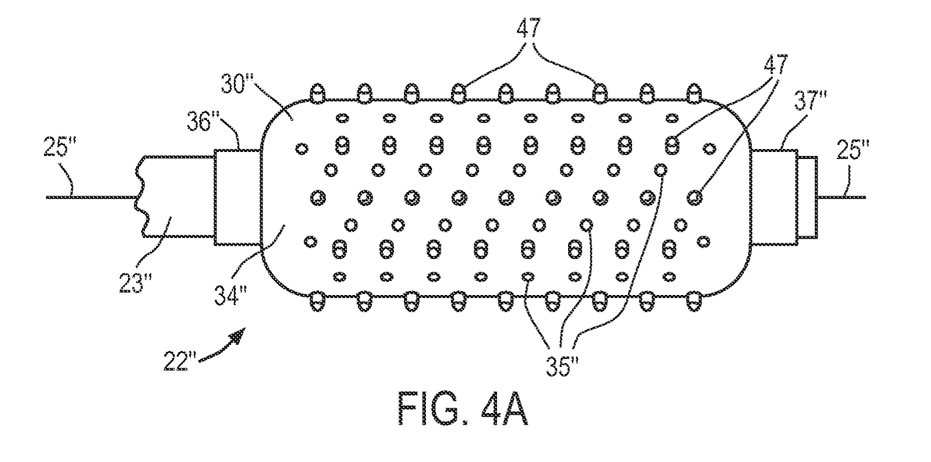
FIGS. 4A and 4B are, respectively, detailed plan and sectional views of the distal region of another alternative catheter constructed in accordance with the principles of the present invention.
Figure 4B:
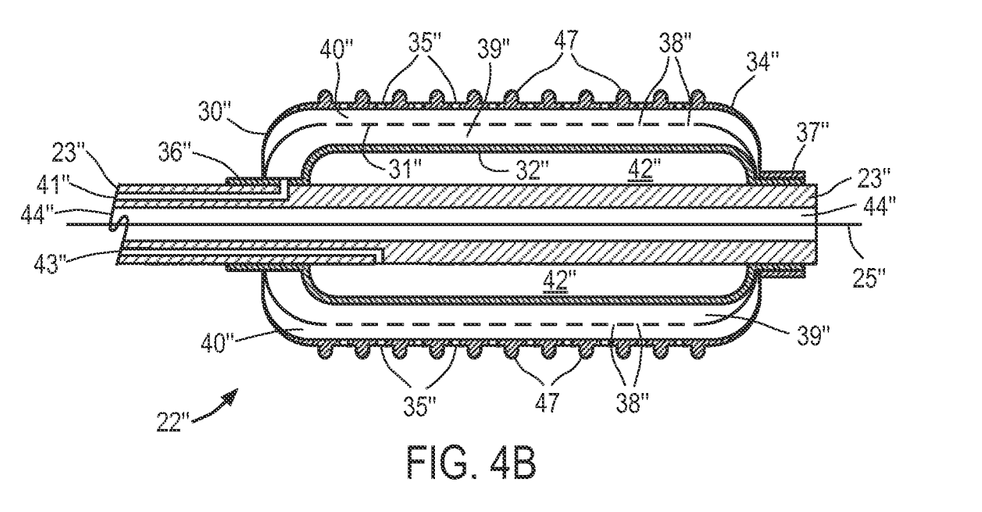

Referring now to FIGS. 4A and 4B, distal region 22" of yet another alternative balloon catheter is constructed similarly to distal region 22 of FIGS. 2A and 2B except that outer balloon 30" further includes multiplicity of solid protrusions 47 extending from exterior surface 34" and interposed between multiplicity of through-wall apertures 35". In the embodiment depicted in FIG. 4A, protrusions 47 and apertures 35" illustratively are arranged in a regular pattern; however, other patterns will readily occur to a person of ordinary skill in the design of balloon catheters. Preferably, apertures 35" are offset from protrusions 47 so as to reduce clogging of the apertures when the protrusions are urged into contact with the luminal surface. In addition, while protrusions 47 are illustratively depicted as substantially circular cylinders having rounded extremities, other configurations, such as rectangular, conical or pyramidal structures also could be used. Protrusions 47 extend from exterior surface 34" so as to create a pocket between exterior surface 34" and the luminal surface when protrusions 47 are urged into contact with the luminal surface. In this manner, protrusions 47 facilitate delivery of therapeutic agents to the luminal surface via the pocket, and reduce the risk that fluent material delivered to the vessel surface will be washed into systemic circulation.

Figure 5A:
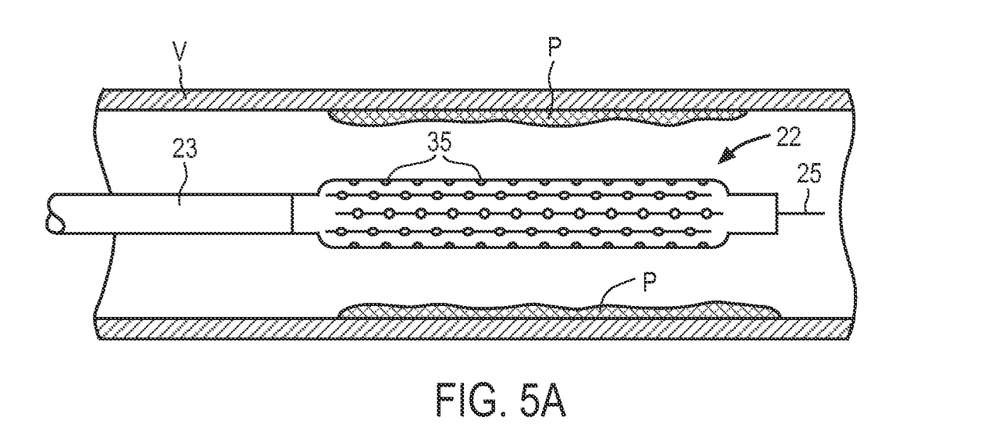
FIGS. 5A to 5C illustrate steps of the using the catheter of FIG. 1 to dilate a plaque-lined vessel and to infuse an antimitotic or other therapeutic agent or drug.
Figure 5B:
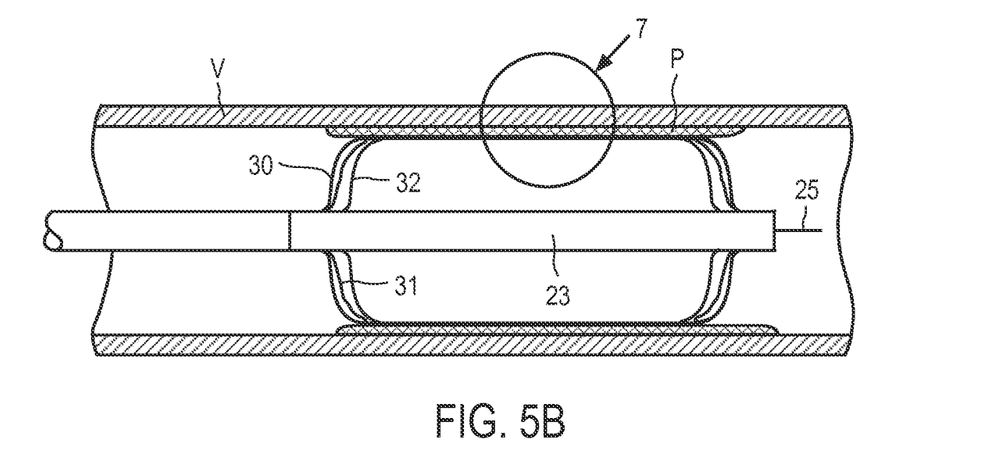
Figure 5C:
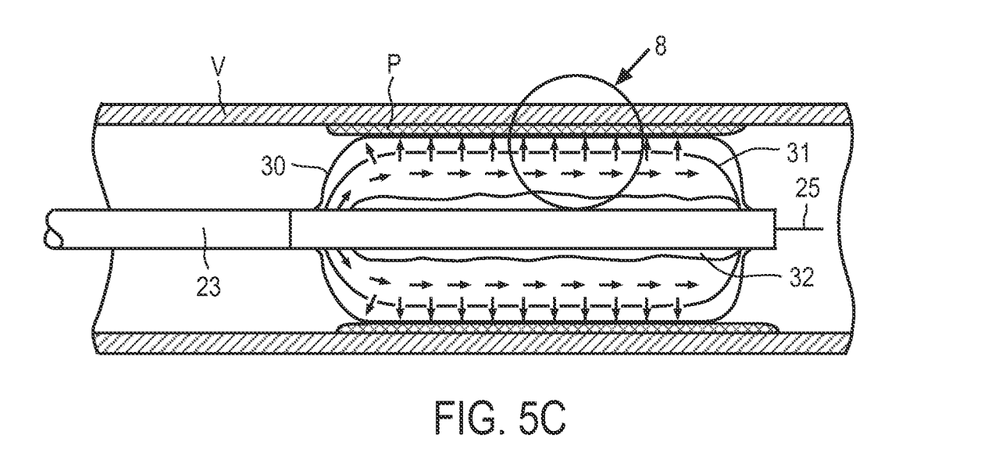

Referring now to FIGS. 5A to 5C, a method of using the catheter of FIGS. 1 and 2 to perform an interventional procedure is described. As will be readily understood to one of ordinary skill in the art, while the method is described for use with the catheter of FIGS. 1 and 2, the alternative catheters of FIGS. 3 and 4 may be used in a similar manner to that described below.

In FIG. 5A, guide wire 25 is placed in the vessel at the location of a lesion or plaque P, or nascent aneurysm, as determined using fluoroscopic imaging, contrast agents and conventional interventional techniques. Catheter 20 then is backloaded onto guide wire 25 by inserting the proximal end of the guide wire into the distal opening of lumen 44. Catheter 20 is advanced through the patient's vasculature until distal region 22 is disposed in the region of interest, as determined using radiopaque markers on catheter shaft 23 and fluoroscopic imaging. When so disposed in patient's vessel V, distal end 22 of catheter 20 will appear as depicted in FIG. 5A. In embodiments protrusions (FIG. 4), during manufacture of the catheter, outer balloon 30' or 30" of the catheter may be wrapped or folded so that protrusions 47 are substantially flush with the remainder of the balloon material, thus preventing the protrusions from snagging or abrading the vessel intima during advancement along guide wire 25 to the location of interest. Alternatively, a delivery sheath (not shown) may be disposed over distal region 22, 22', or 22" of the catheter to present a smooth outer surface for the catheter, and the sheath then may be retracted proximally to expose the distal region once it is at the desired location in vessel V.

Figure 6:
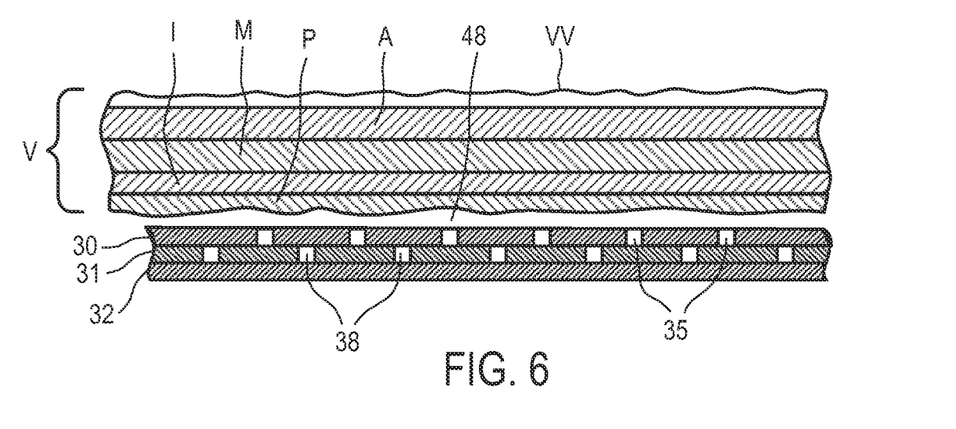
FIG. 6 is a detailed sectional view of the balloons described in FIG. 5.
Figure 7:
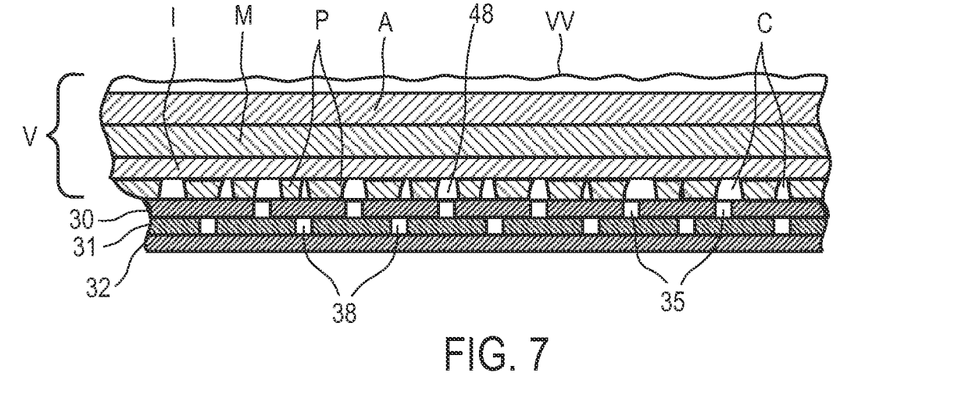
FIG. 7 is a detailed sectional view corresponding to encircled region 7 in FIG. 5B.

Referring now to FIGS. 5B, 6, and 7, a conventional inflator is coupled to inflation port 26 and an inflation medium, such as saline or a saline diluted iodinated contrast agent, is delivered via inflation lumen 43 to inner balloon 32 to cause inner balloon 32 to expand intermediate balloon 31 and outer balloon 30. As shown in FIG. 6, inner balloon 32 may expand intermediate balloon 31 and outer balloon 30 so that pocket 48 is created between outer balloon 30 and plaque P. In such an embodiment, pocket 48 may extend between bumpers 45 and 46 (FIG. 3) or protrusions 47 (FIG. 4) contact plaque P and the intima of the vessel V to dilate the vessel V and crack or disrupt plaque P. In addition, as shown in FIG. 7, inner balloon 32 may expand intermediate balloon 31 and outer balloon 30 into contact with plaque P and the intima of vessel V to dilate the vessel V and disrupt or cause cracks C in the plaque P. As inner balloon 32 expands, it contacts intermediate balloon 31 which contacts outer balloon 30 and causes outer balloon 30 to contact and crack or disrupt plaque P.

In embodiments where the outer balloon includes protrusions (FIG. 4), the protrusions engage plaque at discrete locations and place the plaque in tension, causing it to fracture. One or more therapeutic agents are infused through apertures 35, 35', 35" in outer balloon 30, 30', 30" and contacts the plaque along fracture zones that enable the therapeutic agent to be rapidly taken up by the vessel intima. Because apertures 35" are interposed between the protrusions instead of extending through the protrusions as in prior art systems, compressed plaque at the point of contact of the protrusions is expected not to clog the apertures. It is expected that the foregoing arrangement of solid protrusions and interposed apertures will enable better uptake of therapeutic agents in calcified lesions than has heretofore been achieved.

Referring to FIGS. 6 and 7, it is observed that vessel V comprises three layers: intima I, medial M, and adventitial A, which is supplied by vaso vasorum VV. It is known that the vaso vasorum VV supplies nourishment to vessel V and removes metabolic byproducts resulting from activity of the cells making up the vessel wall. In accordance with one aspect of the present invention, a therapeutic agent is infused into the wall of a vessel V, and preferably into the adventitia A and/or vaso vasorum VV, while also locally reducing flow in the vaso vasorum VV to reduce washout of the therapeutic agent from the adventitia A and vaso vasorum VV. In this manner, the vessel wall serves as a reservoir for the therapeutic agent, so that the infused therapeutic agent or drug is released from the adventitia A back into the medial M and intimal portions I of the vessel wall over a period of months to years, thereby prolonging the therapeutic effect of the infused agent or drug.

The foregoing benefits may be achieved by a number of modes. In one embodiment, the therapeutic agent or drug may be designed so that when activated by supply of energy, e.g., irradiated by ultraviolet light, insonicated with ultrasound energy of a desired frequency, or heated by a resistive or other type of heater, the drug transitions from a fluent form to a gel-like or solid form. In this case, the therapeutic agent will assist in blocking or reducing flow through the vaso vasorum, and reduce the rate at which the therapeutic agent or drug is removed from the selected portion of the vessel wall. Alternatively or in addition, if the therapeutic agent transforms to a gel-like or solid form, it will be less susceptible to erosion. In an alternative embodiment, the deposited energy may cause a component of the therapeutic agent to heat up to cause polymerization or cross-linking of fluent bioactive materials and/or remodel or partially necrose portions of the adventitia or vaso vasorum, thereby locally blocking or reducing flow through the vaso vasorum and producing a reservoir of the therapeutic agent that provides prolonged release. As a further alternative embodiment, the deposited energy may function to enhance uptake of the therapeutic agent through the layers of the vessel wall. As a still further alternative embodiment, the energy may directly cause partial remodeling or necrosis of the adventitia and/or vaso vasorum to produce the reservoir effect noted above.

Figure 8:
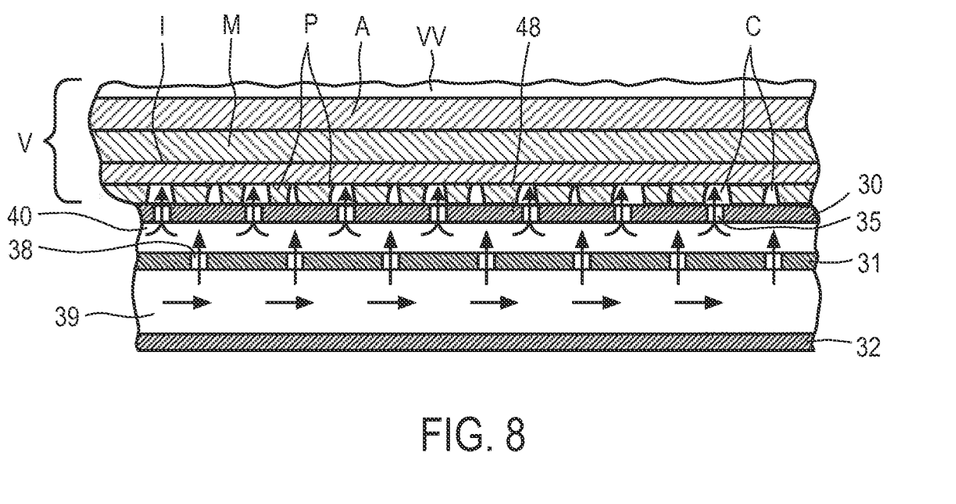
FIG. 8 is a detailed sectional view corresponding to encircled region 8 in FIG. 5C.

Referring now to FIGS. 5C and 8, after inner balloon 32 has been expanded to drive intermediate balloon 31, and outer balloon 30 (and, if present, optional bumpers or protrusions) into contact with the vessel wall, inner balloon 32 is partially or completely deflated. Next, a vial or syringe containing a desired fluent therapeutic agent or drug, (e.g., an anti-mitotic drug such as paclitaxel or sirolimus, angiogenic vector, or stem cells), is coupled to infusion port 27 on proximal end 21 and activated to inject the agent through infusion lumen 41 into annular space 39 between inner balloon 32 and intermediate balloon 31 (see FIG. 2B). As indicated by the arrows in FIG. 5C, the agent passes through apertures 38 in intermediate balloon 31 and into annular space 40 between intermediate balloon 31 and outer balloon 30. Inner balloon 32 may be partially or completely reinflated to cause the therapeutic agent to pass through apertures 38 and into annular space 40 between intermediate balloon 31 and outer balloon 30 before exiting through apertures 35. Because apertures 38 are offset from apertures 35 in outer balloon 30, the agent circulates within annular space 40 before passing through apertures 35 and exiting outer balloon 30. Additionally, because agent moves laterally towards apertures 35, it will be more uniformly distributed around the circumference and along the axial length of the vessel than previously-known single balloon systems. This baffling effect provided by intermediate balloon 31 is expected to reduce jetting of therapeutic agent exiting through apertures 35 of outer balloon 30, thus reducing the potential for vessel dissection.

As depicted in further detail in FIG. 8, the therapeutic agent exits outer balloon into pockets 48 formed between cracks C in plaque and/or between bumpers, if provided. The therapeutic agent exits apertures 35 into pockets 48, where it is expected to gain ready access to the vessel intima through cracks and fractures formed in plaque P during the dilatation step illustrated in FIG. 5B.

As will be apparent to one of ordinary skill in interventional procedures, the rate of infusion of therapeutic agent can be adjusted by varying the pressure at which the agent is supplied from the syringe or vial through infusion port 27, or alternatively by adjusting the degree of inflation of inner balloon 32. By adjusting the latter, the clinician can reduce the volume of annular space 39, reducing the volume of therapeutic agent that must be used during the procedure. In addition, after infusing the therapeutic agent into annular space 39, the clinician may increase the pressure in inner balloon 32 to pressurize annular spaces 39 and 40 and enhance the rate at which therapeutic agent exits apertures 35 and is infused into the vessel wall. Therapeutic agent deposited in pockets 48 preferably is taken up by the cells in the various layers of the wall of vessel V by normal cellular processes, as opposed to traumatically (e.g., by cleaving intercellular connections).

In addition, as will be readily understood to one of ordinary skill in the art, while the balloon catheter is generally described as delivering a therapeutic agent, such as an antimitotic drug, to plaque, the disclosure is not limited thereto. The therapeutic agent may be selected to treat any condition where subintimal injection would be beneficial. For example, the therapeutic agent may be selected for treating a nascent or existing aneurysm when the balloon catheter is delivered proximate to an aneurysm. As another example, the therapeutic agent may be selected to induce angiogenesis, delivered either transluminally or into the sub-intimal space. The therapeutic agent may comprise, for example, one or more regenerative agents, anti-inflammatory agents, anti-allergenic agents, anti-bacterial agents, anti-viral agents, anticholinergic agents, antihistamines, antithrombotic agents, anti-scarring agents, antiproliferative agents, antihypertensive agents, anti-restenosis agents, healing promoting agents, vitamins, proteins, genes, growth factors, cells, stem cells, vectors, RNA, or DNA.

Figure 9:
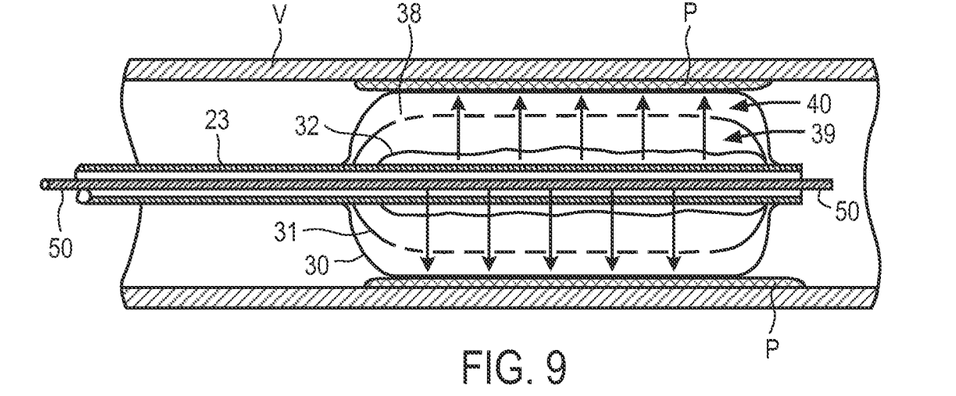
FIG. 9 illustrates a step of inserting an energy delivery wire into the central lumen of the catheter of the present invention during or after the step illustrated in FIG. 5C.

FIG. 9 illustrates a final optional step in accordance with the method of present invention for infusing one or more therapeutic agents into the wall of vessel V. FIG. 9 is similar to FIG. 5C, except that in this step guide wire 25 is removed or retracted, and energy delivery device 50 carrying an energy deposition element is advanced through lumen 44 of catheter 20 and disposed in distal region 22. The energy delivery element, located in the distal region of energy delivery device 50, preferably includes one or more radiopaque markers to indicate positioning of the distal region under fluoroscopic imaging. Energy delivery device 50 preferably has a diameter between 0.018" to 0.035" and may comprise an optical fiber or source for delivering ultraviolet light, ultrasonic energy, or heat. Such devices, and the energy sources that are coupled to the proximal ends of such devices, are known in the art and accordingly are not described in detail here. Of particular importance, however, if a UV light or ultrasonic energy delivery device 50 is employed, catheter 20 preferably is constructed so that a substantial part of the energy is delivered to the vessel wall without being absorbed by the catheter material, and the energy absorbed by the vessel wall has some therapeutic benefit, e.g., activates the therapeutic agent. Energy emitted by energy delivery device 50 and absorbed by vessel V is represented by the solid arrows in FIG. 9.

As discussed above with respect to FIGS. 6 and 7, energy delivery device 50 may provide a therapeutic effect either by facilitating uptake of the therapeutic agent by the vessel wall; by activating the therapeutic agent; by heating the therapeutic agent to effect a change to the vessel wall structure; or by directing delivering energy to selected layers of the vessel wall to cause polymerization or cross-linking of fluent therapeutic agents (e.g., as described in U.S. Pat. No. 5,749,915 to Slepian localized necrosis or remodeling of collagen contained within the vessel wall.

In one embodiment, the deposited energy enhances uptake of the therapeutic agent through the layers of the vessel wall, for example, by activating moieties bound to the effective portion (e.g., anti-proliferative portion) of the therapeutic agent, (e.g., as described in U.S. Pat. No. 4,590,211 to Vorhees). Alternatively, the therapeutic agent or drug may be designed so that when irradiated by ultraviolet light, or insonicated with ultrasound energy of a desired frequency, the drug transitions from a fluent form to a gel-like or solid form. In this case, the therapeutic agent will assist in blocking or reducing flow through the vaso vasorum, and reduce the rate at which the therapeutic agent or drug is removed from the selected portion of the vessel wall. Alternatively or in addition, if the therapeutic agent transforms to a gel-like or solid form, it will be less susceptible to erosion, thereby locally prolonging the therapeutic effect of the agent.

In a further alternative embodiment, the energy deposited by delivery device 50 may cause a component of the therapeutic agent to heat up and remodel collagen of, or partially necrose portions of, the adventitia or vaso vasorum. This effect also may cause a localized blockage that stops or reduces flow through the vaso vasorum and act to produce a localized reservoir of the therapeutic agent that provides prolonged release. As yet another alternative embodiment, the UV or ultrasonic energy may directly cause partial remodeling or necrosis of the adventitia and/or vaso vasorum to create localized blockage of the vaso vasorum to produce the reservoir effect noted above.

Referring again to FIG. 9, energy delivery device 50 may be configured to deliver energy to vessel V during and after, or alternatively only a predetermined interval after, the therapeutic agent is delivered by catheter 20. Once the process of delivering the therapeutic agent into the vessel wall is completed, and the appropriate amount of energy has been delivered to enhance or prolong the therapeutic effect of the therapeutic agent, energy delivery device 50 may be withdrawn. Next, suction may be drawn on infusion lumen 41 to remove any excess therapeutic agent from annular spaces 39 and 40 to collapse intermediate balloon 31 and retract outer balloon 30 away from the vessel wall. In an embodiment where the outer balloon includes protrusions, the outer balloon may be constructed so that, when deflated, the balloon preferentially will fold to enclose the protrusions and reduce the risk of abrading the vessel wall during removal. Alternatively, or in addition, an open-ended sheath (not shown) may be advanced over the exterior surface of catheter shaft 23 and the exterior of outer balloon 30 to facilitate removal of catheter 20. Once catheter 20 is removed from the patient's vasculature, the access site may be closed using standard interventional techniques.

Figure 10A:
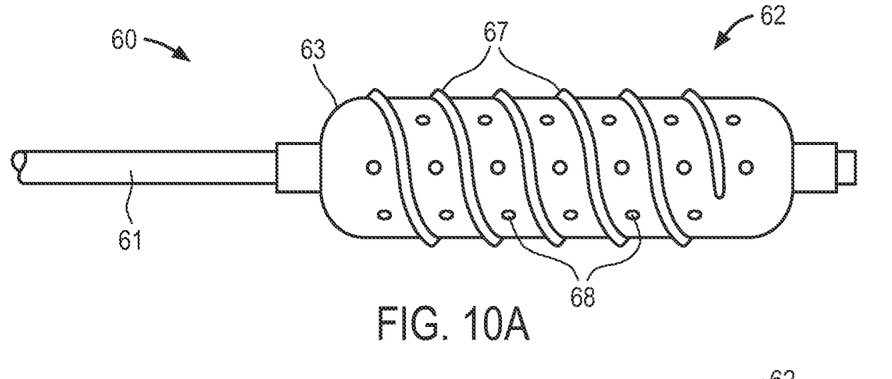
FIGS. 10A and 10B are, respectively, plan and sectional views of an alternative embodiment of the catheter of the present invention.
Figure 10B:
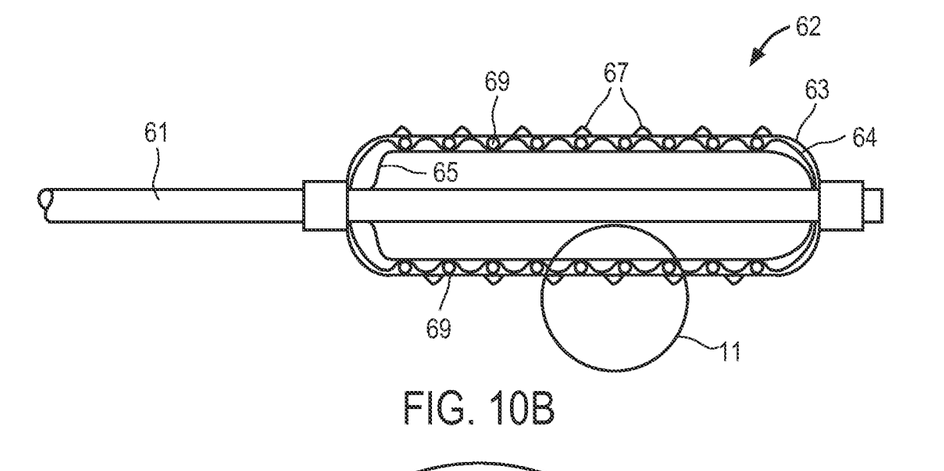
Figure 11:
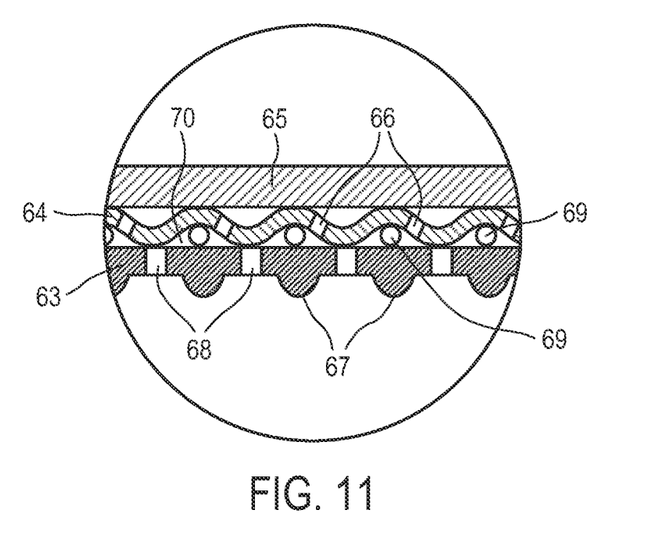
FIG. 11 is a detailed sectional view corresponding to encircled region 11 in FIG. 10B.

Referring now to FIGS. 10A, 10B and 11, an alternative embodiment of apparatus constructed in accordance with the principles of the present invention is described. Catheter 60 includes elongated catheter shaft 61 having distal region 62 and outer balloon 63. The proximal end of catheter shaft 61 is similar in construction to catheter 20 and preferably includes a hemostatic guide wire port, balloon inflation port and infusion port. As shown in FIG. 10B (which corresponds to an inflation state similar to FIG. 2B), distal region 62 includes outer balloon 63, intermediate balloon 64 and inner balloon 65. As for catheter 20 of the preceding embodiment, inner balloon 65 is fluid impermeable and is coupled via an inflation lumen to an inflation port on the proximal end. Likewise, intermediate balloon 64 includes a multiplicity of through-wall apertures 66 (see FIG. 11) and is coupled via an infusion lumen to an infusion port disposed on the proximal end of the catheter. Outer balloon 63 includes one or more spiral protrusions 67 and a multiplicity of through-wall apertures 68.

Catheter 60 differs from the embodiment of FIG. 1 in that the exterior surface of outer balloon 63 includes protrusions 67 arranged as a spiral ridge. In addition, whereas intermediate balloon 64 of the embodiment of FIG. 1 may contain a textured surface to ensure that intermediate balloon 64 does not adhere to outer balloon 63, intermediate balloon 64 in the embodiment of FIGS. 10 and 11 includes a macroscopic feature to prevent such adhesion. In particular, intermediate balloon 64 includes spiral rib 69, preferably comprised of the same material and potentially integrally formed with intermediate balloon 64, disposed on its exterior-facing surface of the intermediate balloon. In this manner, spiral rib 69 contacts the inner surface of outer balloon to ensure that annular space 70 is maintained between intermediate balloon 64 and outer balloon 63 when inner balloon 65 is inflated to urge intermediate balloon 64 and outer balloon 63 into contact with a vessel wall to dilate the vessel and disrupt plaque.

While in the embodiment of FIGS. 10 and 11 protrusions 67 are configured as a spiral ridge having a rounded extremity, it should be understood that other patterns will readily occur to a person of ordinary skill in the design of balloon catheters, such as structures having rectangular, conical or pyramidal cross-sections, as may be desirable to fracture severe calcifications. Similarly, while apertures 68 are depicted as being circular, they may have any other desired shape, such as rectangular, triangular or elliptical. Preferably, apertures 68 are offset from protrusions 67 so as to reduce clogging of the apertures when the protrusions are urged into contact with the luminal surface. Likewise, apertures 66 in intermediate balloon 64 may be offset from apertures 68 in outer balloon 63 to achieve the benefits described above.

Finally, although the macroscopic feature in intermediate balloon 64 is illustratively depicted as comprising spiral rib 69 having a substantially circular cross-section, this feature could have other cross-sections, such as rectangular, elliptical or triangular. In addition, spiral rib 69 need not form a continuous structure, but instead could comprise a multiplicity of discrete structures, similar in shape to protrusions 47 disposed on outer balloon 30" of the embodiment of FIG. 4. For example, intermediate balloon 64 and outer balloon 63 may comprise the same material having the same protrusions disposed on their respective exterior surfaces. In this manner, construction of the distal end of the catheter of the present invention could be simplified, so long as the apertures in the intermediate and outer balloons are staggered or offset to provide the baffle action discussed above.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method for providing intraluminal therapy comprising:
    advancing a distal region of a catheter into a body lumen, the distal region having a fluid impermeable balloon, an intermediate balloon having a first multiplicity of through-wall apertures that encloses the fluid impermeable balloon, and an outer balloon that encloses the intermediate balloon, the outer balloon having a second multiplicity of through-wall apertures offset from the first multiplicity of apertures;
    inflating the fluid impermeable balloon via a fluid introduced into a first space enclosed by the fluid impermeable balloon, the fluid impermeable balloon configured to contact and expand the intermediate balloon against the outer balloon and to expand the outer balloon into contact with a luminal surface of the body lumen to dilate the body lumen;
    introducing a therapeutic agent into a second space between the fluid impermeable balloon and the intermediate balloon;
    passing the therapeutic agent through the first multiplicity of apertures and into a third space, accessible only through the first multiplicity of apertures, between the intermediate balloon and the outer balloon; and
    passing the therapeutic agent from the third space through the second multiplicity of apertures such that the therapeutic agent exits the outer balloon.

2. The method of claim 1, further comprising:
    at least partially deflating the fluid impermeable balloon before introducing the therapeutic agent into the second space; and
    at least partially reinflating the fluid impermeable balloon so that the therapeutic agent passes through the first multiplicity of apertures and into the third space between the intermediate balloon and the outer balloon before exiting through the second multiplicity of apertures.

3. The method of claim 1, further comprising uniformly distributing the therapeutic agent to the luminal surface.

4. The method of claim 1, wherein the catheter shaft further comprises a lumen sized to accept an energy delivery device, the method further comprising advancing an energy delivery element into the distal region.

5. The method of claim 4, further comprising energizing the energy delivery device to deposit energy into the therapeutic agent and the body lumen.

6. The method of claim 5, wherein depositing energy into the therapeutic agent and body lumen activates the therapeutic agent to enhance uptake of the therapeutic agent by the body lumen or creates a localized reservoir of therapeutic agent in the body lumen wall that prolongs a therapeutic effect of the therapeutic agent.

7. The method of claim 1, wherein the therapeutic agent comprises stem cells.

8. The method of claim 1, wherein the therapeutic agent moves laterally within the third space after passing through the first multiplicity of apertures and before exiting through the second multiplicity of apertures.

9. The method of claim 1, wherein the body lumen is a blood vessel and the therapeutic agent is injected into an intima layer of the blood vessel.

10. The method of claim 1, wherein the body lumen is a blood vessel and the therapeutic agent is injected into an adventitia layer or medial layer, or both, of the blood vessel.

11. The method of claim 1, wherein the therapeutic agent comprises one or more regenerative agents, anti-inflammatory agents, anti-allergenic agents, anti-bacterial agents, anti-viral agents, anticholinergic agents, antihistamines, anti-thrombotic agents, anti-scarring agents, antiproliferative agents, antihypertensive agents, anti-restenosis agents, healing promoting agents, vitamins, proteins, genes, growth factors, cells, stem cells, vectors, RNA, DNA, or any combination thereof.

12. The method of claim 1, wherein the therapeutic agent comprises an anti-proliferative drug configured to reduce occurrence of restenosis.

13. The method of claim 1, wherein the therapeutic agent comprises regenerative therapy agents configured to promote angiogenesis.

14. The method of claim 1, wherein contacting the luminal surface of the body lumen disrupts calcified plaque.

15. The method of claim 1, wherein the body lumen comprises a blood vessel.

16. The method of claim 1, wherein the outer balloon is sized and shaped for insertion in coronary vessels.

17. The method of claim 1, wherein the outer balloon is sized and shaped for insertion in peripheral vessels.

18. The method of claim 1, further comprising a multiplicity of protrusions extending from the exterior surface of the outer balloon.

19. The method of claim 18, wherein the second multiplicity of apertures are interposed between individual protrusions in the multiplicity of protrusions.

20. The method of claim 1, further comprising a proximal bumper extending from the exterior surface of the outer balloon around a circumference of a proximal end of the outer balloon and a distal bumper extending from the exterior surface of the outer balloon around the circumference of a distal end of the outer balloon.

\* \* \* \* \*